(12) United States Patent
Orr

(10) Patent No.: US 8,507,468 B2
(45) Date of Patent: Aug. 13, 2013

(54) INTRANASAL ANTI-CONVULSIVE COMPOSITIONS AND METHODS

(76) Inventor: Robert Orr, San Clemente, CA (US)

( * ) Notice: Subject to any disclaimer, the term of this patent is extended or adjusted under 35 U.S.C. 154(b) by 510 days.

(21) Appl. No.: 12/244,093

(22) Filed: Oct. 2, 2008

(65) Prior Publication Data

US 2009/0088421 A1    Apr. 2, 2009

Related U.S. Application Data

(60) Provisional application No. 60/976,841, filed on Oct. 2, 2007.

(51) Int. Cl.
*A01N 43/00* (2006.01)
*A61K 31/33* (2006.01)

(52) U.S. Cl.
USPC .......................................... 514/183; 514/221

(58) Field of Classification Search
None
See application file for complete search history.

(56) References Cited

U.S. PATENT DOCUMENTS

| | | | |
|---|---|---|---|
| 4,863,720 | A | 9/1989 | Burghart et al. |
| 5,428,006 | A | 6/1995 | Bechgaard et al. |
| RE36,744 | E | 6/2000 | Goldberg |
| 7,132,112 | B2 | 11/2006 | Choi et al. |
| 7,745,430 | B2 * | 6/2010 | Kim et al. ............. 514/220 |
| 2004/0028617 | A1 * | 2/2004 | Choi et al. ............. 424/45 |
| 2005/0153956 | A1 * | 7/2005 | Merkus ............. 514/221 |
| 2007/0021411 | A1 | 1/2007 | Cloyd et al. |
| 2007/0208011 | A1 | 9/2007 | Cloyd et al. |

FOREIGN PATENT DOCUMENTS

| | | |
|---|---|---|
| EP | 2030610 A1 * | 3/2009 |
| WO | WO 2005067893 A2 * | 7/2005 |

OTHER PUBLICATIONS

Thomas Wetting kinetics of modified polyimides surfaces: interaction with polar solvents, Journal of Colloid interface Science vol. 279, 2004, pp. 515-522.*
Parmasolve product specification, 2000.*
Jouyban-Gharamaleki et al, Chem. Pharm. Bull. 48(12)1866-1871 (2000).*
Warden et al, Pre-hospital Emergency Care, 2006, vol. 10, No. 4, pp. 463-467.*

* cited by examiner

*Primary Examiner* — Brandon Fetterolf
*Assistant Examiner* — Jean Cornet
(74) *Attorney, Agent, or Firm* — Fish & Associates, PC

(57) ABSTRACT

Contemplated pharmaceutical compositions comprise a benzodiazepine anti-convulsive compound for intranasal administration in a single phase, multi-component solvent system with water content of at least 15 vol % and a benzodiazepine concentration of at least 30 mg/ml. It is noted that contrary to common expectation, the concentration of the anti-convulsive compound was increased by increasing water content in the multi-component solvent. Moreover, the anti-convulsive compound remained chemically stable and substantially completely dissolved over large periods of time. Thus, stable and highly concentrated spray formulations for intranasal administration could be prepared having sufficiently high concentrations of the anti-convulsive compounds that now allow single spray administration to achieve clinically relevant dosages.

7 Claims, 8 Drawing Sheets

| 1 | | | |
|---|---|---|---|
| active amount (mg) | | Ins. | 120.6 |
| Solvent | % | | ml |
| NMP | 50.00% | | 0.3 |
| PEG 200 | 0.00% | | 0 |
| Ethanol | 50.00% | | 0.3 |
| water | 0.00% | | 0 |
| | 100% | | 0.6 |

| 2 | | | |
|---|---|---|---|
| active amount (mg) | | Ins. | 119.6 |
| Solvent | % | | ml |
| NMP | 42.86% | | 0.6 |
| PEG 200 | 0.00% | | 0 |
| Ethanol | 21.43% | | 0.3 |
| water | 35.71% | | 0.5 |
| | 100% | | 1.4 |

| 3 | | | |
|---|---|---|---|
| active amount (mg) | | Ins. | 119.9 |
| Solvent | % | | ml |
| NMP | 33.33% | | 0.3 |
| PEG 200 | 0.00% | | 0 |
| Ethanol | 66.67% | | 0.6 |
| water | 0.00% | | 0 |
| | 100% | | 0.9 |

| 4 | | | |
|---|---|---|---|
| active amount (mg) | | Ins. | 120.0 |
| Solvent | % | | ml |
| NMP | 35.29% | | 0.6 |
| PEG 200 | 0.00% | | 0 |
| Ethanol | 35.29% | | 0.6 |
| water | 29.41% | | 0.5 |
| | 100% | | 1.7 |

| 5 | | | |
|---|---|---|---|
| active amount (mg) | | Ins. | 120.8 |
| Solvent | % | | ml |
| NMP | 25.00% | | 0.3 |
| PEG 200 | 50.00% | | 0.6 |
| Ethanol | 25.00% | | 0.3 |
| water | 0.00% | | 0 |
| | 100% | | 1.2 |

| 6 | | | |
|---|---|---|---|
| active amount (mg) | | Ins. | 120.6 |
| Solvent | % | | ml |
| NMP | 15.79% | | 0.3 |
| PEG 200 | 31.58% | | 0.6 |
| Ethanol | 31.58% | | 0.6 |
| water | 21.05% | | 0.4 |
| | 100% | | 1.9 |

| 7 | | | |
|---|---|---|---|
| active amount (mg) | | Ins. | 120.7 |
| Solvent | % | | ml |
| NMP | 24.00% | | 0.6 |
| PEG 200 | 24.00% | | 0.6 |
| Ethanol | 24.00% | | 0.6 |
| water | 28.00% | | 0.7 |
| | 100% | | 2.5 |

| 8 | | | |
|---|---|---|---|
| active amount (mg) | | Ins. | 119.7 |
| Solvent | % | | ml |
| NMP | 13.04% | | 0.3 |
| PEG 200 | 39.13% | | 0.9 |
| Ethanol | 26.09% | | 0.6 |
| water | 21.74% | | 0.5 |
| | 100% | | 2.3 |

| 9 | | | |
|---|---|---|---|
| active amount (mg) | | Ins. | 120.7 |
| Solvent | % | | ml |
| NMP | 23.08% | | 0.6 |
| PEG 200 | 34.62% | | 0.9 |
| Ethanol | 23.08% | | 0.6 |
| water | 19.23% | | 0.5 |
| | 100% | | 2.6 |

| active amount (mg) | Ins. | 119.7 |
|---|---|---|
| Solvent | % | ml |
| NMP | 10.00% | 0.3 |
| Pr. Glycol | 20.00% | 0.6 |
| PEG 200 | 0.00% | 0 |
| Ethanol | 20.00% | 0.6 |
| water | 50.00% | 1.5 |
| | 100% | 3.0 |

11

| active amount (mg) | Ins. | 121.1 |
|---|---|---|
| Solvent | % | ml |
| NMP | 5.00% | 0.15 |
| Pr. Glycol | 20.00% | 0.6 |
| PEG 200 | 10.00% | 0.3 |
| Ethanol | 10.00% | 0.3 |
| water | 55.00% | 1.65 |
| | 100% | 3.0 |

12

| active amount (mg) | Ins. | 119.7 |
|---|---|---|
| Solvent | % | ml |
| NMP | 5.00% | 0.15 |
| Pr. Glycol | 20.00% | 0.6 |
| PEG 200 | 20.00% | 0.6 |
| Ethanol | 20.00% | 0.6 |
| water | 35.00% | 1.05 |
| | 100% | 3.0 |

13

| active amount (mg) | Ins. | 119.7 |
|---|---|---|
| Solvent | % | ml |
| NMP | 5.00% | 0.15 |
| Pr. Glycol | 20.00% | 0.6 |
| PEG 200 | 20.00% | 0.6 |
| Ethanol | 40.00% | 1.2 |
| water | 15.00% | 0.45 |
| | 100% | 3.0 |

14

| active amount (mg) | Ins. | 120.7 |
|---|---|---|
| Solvent | % | ml |
| NMP | 20.00% | 0.6 |
| Pr. Glycol | 0.00% | 0 |
| PEG 200 | 30.00% | 0.9 |
| Ethanol | 33.33% | 1 |
| water | 16.67% | 0.5 |
| | 100% | 3.0 |

15

| active amount (mg) | Ins. | 120.9 |
|---|---|---|
| Solvent | % | ml |
| NMP | 15.00% | 0.45 |
| Pr. Glycol | 0.00% | 0 |
| PEG 200 | 30.00% | 0.9 |
| Ethanol | 40.00% | 1.2 |
| water | 15.00% | 0.45 |
| | 100% | 3.0 |

16

| active amount (mg) | Ins. | 120.9 |
|---|---|---|
| Solvent | % | ml |
| NMP | 20.48% | 0.635 |
| Pr. Glycol | 0.00% | 0 |
| PEG 200 | 28.06% | 0.87 |
| Ethanol | 37.42% | 1.16 |
| water | 14.03% | 0.435 |
| | 100% | 3.1 |

17

| active amount (mg) | Ins. | 120.8 |
|---|---|---|
| Solvent | % | ml |
| NMP | 20.00% | 0.6 |
| Pr. Glycol | 0.00% | 0 |
| PEG 200 | 20.00% | 0.6 |
| Ethanol | 45.00% | 1.35 |
| water | 15.00% | 0.45 |
| | 100% | 3.0 |

18

| active amount (mg) | Ins. | 120.7 |
|---|---|---|
| Solvent | % | ml |
| NMP | 17.50% | 0.525 |
| Pr. Glycol | 0.00% | 0 |
| PEG 200 | 20.00% | 0.6 |
| Ethanol | 47.50% | 1.425 |
| water | 15.00% | 0.45 |
| | 100.0% | 3.0 |

Figure 1B

19 — active amount (mg): 119.6

| Solvent | S % | ml |
|---|---|---|
| NMP | 15.00% | 0.45 |
| Pr. Glycol | 0.00% | 0 |
| PEG 200 | 20.00% | 0.6 |
| Ethanol | 50.00% | 1.5 |
| water | 15.00% | 0.45 |
| | 100.0% | 3.0 |

20 — active amount (mg): 119.7

| Solvent | S % | ml |
|---|---|---|
| NMP | 20.00% | 0.6 |
| Pr. Glycol | 0.00% | 0 |
| PEG 200 | 15.00% | 0.45 |
| Ethanol | 45.00% | 1.35 |
| water | 20.00% | 0.6 |
| | 100.0% | 3.0 |

21 — active amount (mg): 121.8

| Solvent | S % | ml |
|---|---|---|
| NMP | 20.00% | 0.6 |
| Pr. Glycol | 0.00% | 0 |
| PEG 200 | 17.50% | 0.525 |
| Ethanol | 45.00% | 1.35 |
| water | 17.50% | 0.525 |
| | 100.0% | 3.0 |

22 — active amount (mg): 120.2

| Solvent | S/NCS % | ml | g |
|---|---|---|---|
| NMP | 0.00% | 0 | |
| Eth. Lact. | 15.00% | 0.45 | 0.4646 |
| PEG 200 | 20.00% | 0.6 | 0.6660 |
| Ethanol | 50.00% | 1.5 | 1.1835 |
| water | 15.00% | 0.45 | 0.4500 |
| | 100.0% | 3.0 | |

23 — active amount (mg): 119.8

| Solvent | S/NCS % | ml | g |
|---|---|---|---|
| NMP | 0.00% | 0 | |
| Eth. Lact. | 17.50% | 0.53 | 0.5422 |
| PEG 200 | 20.00% | 0.6 | 0.6660 |
| Ethanol | 42.50% | 1.28 | 1.0060 |
| water | 20.00% | 0.6 | 0.6030 |
| | 100.0% | 3.0 | |

24 — active amount (mg): 119.6

| Solvent | S/NCS % | ml | g |
|---|---|---|---|
| NMP | 0.00% | 0 | |
| Eth. Lact. | 20.00% | 0.6 | 0.6197 |
| PEG 200 | 20.00% | 0.6 | 0.6660 |
| Ethanol | 42.50% | 1.28 | 1.0060 |
| water | 17.50% | 0.53 | 0.5250 |
| | 100.0% | 3.0 | |

25 — active amount (mg): 120.4

| Solvent | S/NCS % | ml | g |
|---|---|---|---|
| NMP | 0.00% | 0 | |
| Eth. Lact. | 20.00% | 0.6 | 0.6197 |
| PEG 200 | 20.00% | 0.6 | 0.6660 |
| Ethanol | 45.00% | 1.35 | 1.0652 |
| water | 15.00% | 0.45 | 0.4500 |
| | 100.0% | 3.0 | |

26 — active amount (mg): 121.0

| Solvent | S/NCS % | ml | g |
|---|---|---|---|
| NMP | 0.00% | 0 | |
| Eth. Lact. | 20.00% | 0.6 | 0.6197 |
| PEG 200 | 20.00% | 0.6 | 0.6660 |
| Ethanol | 40.00% | 1.2 | 0.9468 |
| water | 20.00% | 0.6 | 0.6000 |
| | 100.0% | 3.0 | |

27 — active amount (mg): 120.6

| Solvent | S/NCS % | ml | g |
|---|---|---|---|
| NMP | 0.00% | 0 | |
| Eth. Lact. | 20.00% | 0.6 | 0.6197 |
| PEG 200 | 20.00% | 0.6 | 0.6660 |
| Ethanol | 37.50% | 1.13 | 0.8876 |
| water | 22.50% | 0.68 | 0.6750 |
| | 100.0% | 3.0 | |

Figure 1C

| 28 active amount (mg) | lns. | | 121.1 |
|---|---|---|---|
| Solvent | % | ml | g |
| NMP | 0.00% | 0 | |
| Eth. Lact. | 20.00% | 0.6 | 0.6197 |
| PEG 200 | 0.00% | 0 | 0.0000 |
| Ethanol | 60.00% | 1.8 | 1.4202 |
| water | 20.00% | 0.6 | 0.6000 |
| | 100.0% | 3.0 | |

| 29 active amount (mg) | lns. | | 121.7 |
|---|---|---|---|
| Solvent | % | ml | g |
| NMP | 0.00% | 0 | |
| Eth. Lact. | 20.00% | 0.6 | 0.6197 |
| PEG 200 | 0.00% | 0 | 0.0000 |
| Ethanol | 50.00% | 1.5 | 1.1835 |
| water | 30.00% | 0.9 | 0.9000 |
| | 100.0% | 3.0 | |

| 30 active amount (mg) | lns. | | 120.7 |
|---|---|---|---|
| Solvent | % | ml | g |
| NMP | 0.00% | 0 | |
| Eth. Lact. | 20.00% | 0.6 | 0.6197 |
| PEG 200 | 0.00% | 0 | 0.0000 |
| Ethanol | 40.00% | 1.2 | 0.9468 |
| water | 40.00% | 1.2 | 1.2000 |
| | 100.0% | 3.0 | |

| 31 active amount (mg) | lns. | | 121.2 |
|---|---|---|---|
| Solvent | % | ml | g |
| NMP | 30.00% | 0.9 | 0.9295 |
| Eth. Lact. | 0.00% | 0 | 0.0000 |
| PEG 200 | 0.00% | 0 | 0.0000 |
| Ethanol | 50.00% | 1.5 | 1.1835 |
| water | 20.00% | 0.6 | 0.6000 |
| | 100.0% | 3.0 | |

| 32 active amount (mg) | SNCS | | 118.3 |
|---|---|---|---|
| Solvent | % | ml | g |
| NMP | 35.00% | 1.05 | 1.0844 |
| Eth. Lact. | 0.00% | 0 | 0.0000 |
| PEG 200 | 0.00% | 0 | 0.0000 |
| Ethanol | 35.00% | 1.05 | 0.8285 |
| water | 30.00% | 0.9 | 0.9000 |
| | 100.0% | 3.0 | |

| 33 active amount (mg) | lns. | | 118.5 |
|---|---|---|---|
| Solvent | % | ml | g |
| NMP | 40.00% | 1.2 | 1.2394 |
| Eth. Lact. | 0.00% | 0 | 0.0000 |
| PEG 200 | 0.00% | 0 | 0.0000 |
| Ethanol | 30.00% | 0.9 | 0.7101 |
| water | 30.00% | 0.9 | 0.9000 |
| | 100.0% | 3.0 | |

| 34 active amount (mg) | lns. | | 119.9 |
|---|---|---|---|
| Solvent | % | ml | g |
| NMP | 10.00% | 0.3 | |
| Eth. Lact. | 20.00% | 0.6 | 0.6197 |
| PEG 200 | 0.00% | 0 | 0.0000 |
| Ethanol | 40.00% | 1.2 | 0.9468 |
| water | 30.00% | 0.9 | 0.9000 |
| | 100.0% | 3.0 | |

| 35 active amount (mg) | lns. | | 120.0 |
|---|---|---|---|
| Solvent | % | ml | g |
| NMP | 20.00% | 0.6 | |
| Eth. Lact. | 15.00% | 0.45 | 0.4648 |
| PEG 200 | 0.00% | 0 | 0.0000 |
| Ethanol | 30.00% | 0.9 | 0.7101 |
| water | 35.00% | 1.05 | 1.0500 |
| | 100.0% | 3.0 | |

| 36 active amount (mg) | lns. | | 122.5 |
|---|---|---|---|
| Solvent | % | ml | g |
| NMP | 30.00% | 0.9 | 0.3098 |
| Eth. Lact. | 10.00% | 0.3 | 0.0000 |
| PEG 200 | 0.00% | 0 | 0.0000 |
| Ethanol | 20.00% | 0.6 | 0.4734 |
| water | 40.00% | 1.2 | 1.2000 |
| | 100.0% | 3.0 | |

| active amount (mg) | S/NCS | | 119.5 |
|---|---|---|---|
| Solvent | % | ml | g |
| NMP | 0.00% | 0 | 0.0000 |
| Eth. Lact. | 36.67% | 1.1 | 1.1361 |
| PEG 200 | 0.00% | 0 | 0.0000 |
| Ethanol | 33.33% | 1 | 0.7890 |
| water | 30.00% | 0.9 | 0.9000 |
|  | 100.0% | 3.0 | |

38

| active amount (mg) | Ins. | | 116.9 |
|---|---|---|---|
| Solvent | % | ml | g |
| NMP | 36.67% | 1.1 | 0.0000 |
| Eth. Lact. | 0.00% | 0 | 0.0000 |
| PEG 200 | 0.00% | 0 | 0.0000 |
| Ethanol | 33.33% | 1 | 0.7890 |
| water | 30.00% | 0.9 | 0.9000 |
|  | 100.0% | 3.0 | |

39

| active amount (mg) | Ins. | | 121.7 |
|---|---|---|---|
| Solvent | % | ml | g |
| NMP | 30.00% | 0.9 | 0.9295 |
| Eth. Lact. | 30.00% | 0.9 | 0.0000 |
| PEG 200 | 0.00% | 0 | 0.0000 |
| Ethanol | 0.00% | 0 | 0.0000 |
| water | 40.00% | 1.2 | 1.2000 |
|  | 100.0% | 3.0 | |

40

| active amount (mg) | Ins. | | 120.5 |
|---|---|---|---|
| Solvent | % | ml | g |
| NMP | 32.50% | 0.975 | 1.0070 |
| Eth. Lact. | 32.50% | 0.975 | 0.9295 |
| PEG 200 | 0.00% | 0 | 0.0000 |
| Ethanol | 0.00% | 0 | 0.0000 |
| water | 35.00% | 1.05 | 1.0500 |
|  | 100.0% | 3.0 | |

41

| active amount (mg) | S/NCS | | 121.6 |
|---|---|---|---|
| Solvent | % | ml | g |
| NMP | 30.00% | 0.9 | 0.9295 |
| Eth. Lact. | 30.00% | 0.9 | 0.0000 |
| PEG 200 | 0.00% | 0 | 0.0000 |
| Ethanol | 0.00% | 0 | 0.0000 |
| POEc 30%/water | 40.00% | 1.2 | 1.2000 |
|  | 100.0% | 3.0 | |

42

| active amount (mg) | Ins. | | 122.5 |
|---|---|---|---|
| Solvent | % | ml | g |
| NMP | 25.00% | 0.75 | 0.7746 |
| Eth. Lact. | 25.00% | 0.75 | 0.0000 |
| PEG 200 | 0.00% | 0 | 0.0000 |
| Ethanol | 0.00% | 0 | 0.0000 |
| POEc 30%/water | 50.00% | 1.5 | 1.5000 |
|  | 100.0% | 3.0 | |

43

| active amount (mg) | Ins. | | 119.3 |
|---|---|---|---|
| Solvent | % | ml | g |
| DMSO | 30.00% | 0.900 | 0.9855 |
| Eth. Lact. | 30.00% | 0.9 | 0.9295 |
| PEG 200 | 0.00% | 0 | 0.0000 |
| Ethanol | 0.00% | 0 | 0.0000 |
| water | 40.00% | 1.2 | 1.2000 |
|  | 100.0% | 3.0 | |

44

| active amount (mg) | Ins. | | 122.5 |
|---|---|---|---|
| Solvent | % | ml | g 1.07 |
| DMSO | 32.50% | 0.975 | 1.0070 |
| Eth. Lact. | 32.50% | 0.975 | 0.0000 |
| PEG 200 | 0.00% | 0.000 | 0.0000 |
| Ethanol | 0.00% | 0.000 | 0.0000 |
| POEc 30%/water | 35.00% | 1.050 | 1.0500 |
|  | 100.0% | 3.0 | |

45

| active amount (mg) | Ins. | | 120.5 |
|---|---|---|---|
| Solvent | % | ml | g |
| DMSO | 30.00% | 0.9 | 0.9295 |
| Eth. Lact. | 30.00% | 0.9 | 0.0000 |
| PEG 200 | 0.00% | 0 | 0.0000 |
| Ethanol | 0.00% | 0 | 0.0000 |
| POEc 30%/water | 40.00% | 1.2 | 1.2000 |
|  | 100.0% | 3.0 | |

| 46 active amount (mg) | | SfNCS | 120.1 |
|---|---|---|---|
| Solvent | | % | ml | g |
| NMP | | 29.87% | 0.900 | 0.8397 |
| Eth. Lact. | | 27.87% | 0.8397 | 0.0000 |
| PEG 200 | | 0.00% | 0 | 0.0000 |
| Ethanol | | 0.00% | 0 | 0.0000 |
| water | | 29.87% | 0.9 | 0.9000 |
| POEc | | 12.40% | 0.3737 | 0.386 |
| | | 100.0% | 3.0 | |

| 47 active amount (mg) | | Ins. | 120.9 |
|---|---|---|---|
| Solvent | | % | ml | g |
| NMP | | 30.00% | 0.900 | 0.6847 |
| Eth. Lact. | | 22.10% | 0.685 | 0.0000 |
| PEG 200 | | 0.00% | 0.000 | 0.0000 |
| Ethanol | | 0.00% | 0.000 | 0.0000 |
| water | | 35.00% | 1.050 | 1.0500 |
| POEc | | 12.87% | 0.374 | 0.386 |
| | | 100.0% | 3.0 | |

| 48 active amount (mg) | | Ins. | 400 |
|---|---|---|---|
| Solvent | | % | ml | g |
| NMP | | 30.00% | 0.6 | 0.0000 |
| PEG 200 | | 0.00% | 0 | 1.5540 |
| Ethanol | | 70.00% | 1.4 | 0.0000 |
| water | | 0.00% | 0 | 0.0000 |
| POEc | | | 2.0 | |
| | | 100.0% | | |

| 49 active amount (mg) | | Ins. | 400 |
|---|---|---|---|
| Solvent | | % | ml | g |
| NMP | | 40.00% | 0.800 | 0.0000 |
| PEG 200 | | 0.00% | 0 | 1.3320 |
| Ethanol | | 60.00% | 1.2 | 0.0000 |
| water | | 0.00% | 0 | 0.0000 |
| POEc | | | 2.0 | 0.386 |
| | | 100.0% | | |

| 50 active amount (mg) | | | 400 |
|---|---|---|---|
| Solvent | | % | ml | g |
| NMP | | 50.00% | 1.000 | 0.0000 |
| PEG 200 | | 50.00% | 1.000 | 1.1100 |
| Ethanol | | 0.00% | 0.000 | 0.0000 |
| water | | 0.00% | 0.000 | 0.0000 |
| POEc | | | 2.0 | 0.386 |
| | | 100.0% | | |

| 51 active amount (mg) | | Ins. | 120 |
|---|---|---|---|
| Solvent | | % | ml | g |
| NMP | | 30.00% | 0.9 | 0.0000 |
| PEG 200 | | 0.00% | 0 | 0.0000 |
| Ethanol | | 30.00% | 0.9 | 0.7101 |
| water | | 30.00% | 0.9 | 0.9000 |
| POEc | | 10.00% | 0.3 | 0.3 |
| | | 100.0% | 3.0 | |

| 52 active amount (mg) | | | 357.0 |
|---|---|---|---|
| Solvent | | % | ml | g |
| NMP | | 29.94% | 2.7 | 0.0000 |
| PEG 200 | | 5.08% | 0.4581 | 0.5085 |
| Ethanol | | 29.57% | 2.6664 | 2.1038 |
| water | | 25.47% | 2.2970 | 2.2970 |
| POEc | | 9.94% | 0.896 | 0.9408 |
| | | 100.0% | 9.0 | |

| 53 active amount (mg) | | Ins. | 363.7 |
|---|---|---|---|
| Solvent | | % | ml | g |
| NMP | | 28.11% | 2.7 | 0.0000 |
| PEG 200 | | 4.83% | 0.46 | 0.5148 |
| Ethanol | | 28.27% | 2.72 | 2.1426 |
| water | | 29.65% | 2.85 | 2.8480 |
| POEc | | 9.15% | 0.88 | 0.9225 |
| | | 100.0% | 9.6 | |

| 54 active amount (mg) | | Inc. | 120 |
|---|---|---|---|
| Solvent | | % | ml | g |
| NMP | | 30.00% | 0.9 | 0.0000 |
| PEG 200 | | 5.00% | 0.15 | 0.1665 |
| Ethanol | | 20.00% | 0.6 | 0.4734 |
| water | | 30.00% | 0.9 | 0.9000 |
| POEc | | 15.00% | 0.45 | 0.3 |
| | | 100.0% | 3.0 | |

| 64 | | | |
|---|---|---|---|
| active amount (mg) | | | 120.3 |
| | Ins. | | |
| Solvent | % | ml | g |
| NMP | 32.36% | 0.8736 | 0.8736 |
| PEG 200 | 0.00% | 0.00 | 0.0000 |
| Ethanol | 33.18% | 0.90 | 0.7068 |
| water | 27.76% | 0.75 | 0.7494 |
| POEc | 0.00% | 0.00 | 0.0000 |
| Almond Oil | 6.70% | 0.1808 | 0.1645 |
| | 100.0% | 2.7 | |

| 65 | | | |
|---|---|---|---|
| active amount (mg) | | | 120.0 |
| | Ins. | | |
| Solvent | % | ml | g |
| NMP | 29.33% | 0.88 | 0.8794 |
| PEG 200 | 0.00% | 0.00 | 0.0000 |
| Ethanol | 29.95% | 0.90 | 0.7084 |
| water | 25.07% | 0.75 | 0.7516 |
| Glycofurol | 9.57% | 0.29 | 0.3012 |
| Almond Oil | 6.09% | 0.18 | 0.1661 |
| | 100.0% | 3.0 | |

Figure 1H

INTRANASAL ANTI-CONVULSIVE COMPOSITIONS AND METHODS

This application claims priority to copending U.S. provisional application with the Ser. No. 60/976,841, which was filed Oct. 2, 2007, and which is incorporated by reference herein.

FIELD OF THE INVENTION

The field of the invention is intranasal formulations for various pharmaceutical agents, and especially intranasal formulations of diazepam and chemically related medications for treatment of seizures.

BACKGROUND OF THE INVENTION

Diazepam (1-methyl-5-phenyl-7-chloro-1,3-dihydro-2H-1,4-benzodiazepin-2-one), a pharmaceutical agent among a class of compounds known as benzodiazepines, is an effective anticonvulsant in the emergency treatment of epileptic seizures. Most typically, diazepam is intravenously administered in a clinical setting at a dose of 5 to 10 mg. Alternatively, diazepam can also be rectally administered (e.g., using Diastat®, Valeant Pharmaceuticals), which may be advantageous for home administration. However, as seizures are generally unpredictable in occurrence, there is a continuous need for simple administration of diazepam that does not require a trained caregiver or a socially awkward route. For example, an atomized delivery of liquid medication to the nasal mucosa (intranasal) may offer a more convenient and effective means of delivery, with the added benefit of rapid onset of action.

An intranasal (IN) dose of 10 to 15 mg diazepam is in most instances appropriate to calm a normal adult suffering from an epileptic seizure. The maximum liquid volume that can be delivered as an atomized nasal spray is about 150 μl per nostril. If one actuation per nostril can be administered, this provides a total volume of 300 μl in which an effective dose could be delivered. The problem, however, with conventional intranasal delivery is the relatively poor solubility of diazepam in aqueous systems (e.g., less than 1 mg/ml in water) that would commonly be used for intranasal delivery. An additional problem of intranasal delivery is that the formulation must be composed of solvents and Solvent that are adequately tolerated, that have a recognized safety profile for use in human, and can be delivered as an atomized spray.

It is therefore not surprising that various intranasal delivery methods for diazepam failed to produce promising results. For example, Goldberg (U.S. Pat. No. 4,950,664/U.S. RE036744) describes a composition of a benzodiazepine in a pharmaceutically acceptable nasal carrier in which the salts of the benzodiazepine were dissolved in water at very low concentration, or in which dissolved triazolam was present in a PEG (polyethylene glycol) formulation at about 3 mg/ml. Both would require multiple nasal sprays into each nostril to deliver the required 10 mg diazepam to be effective. Even if one would administer multiple sprays, effective dosages would likely not be achieved as excess fluid would drain from the nasal mucosa faster than the diazepam can be absorbed.

Another example is described by Choi (U.S. Pat. No. 7,132,112). Here, a composition of diazepam for intranasal administration was proposed in the management of epileptic seizure. However, Choi's composition contains multiple organic solvents, a detergent, and only a minor fraction of water to achieve relatively moderate diazepam concentrations (e.g., 20 mg/ml). Higher apparent concentrations were achieved by Cloyd et. al. (U.S. Appl. Nos. 2007/0208011 and 2007/0021411), teaching a composition of diazepam in a supersaturated solution of glycofurol for intranasal administration in the management of epileptic seizure. However, since Cloyd's solution is supersaturated, it is physically unstable. Diazepam will precipitate over time at room temperature within hours and will thus present difficulties in atomization and delivery in the desired dosage. Further, glycofurol does not have a recognized safety status by the U.S. Food and Drug Administration for use in pharmaceutical formulations.

Therefore, while various compositions and methods for intranasal delivery of diazepam are known in the art, there is still a need for improved intranasal pharmaceutical agents for treatment and management of epileptic seizure.

BRIEF DESCRIPTION OF THE DRAWING

FIGS. 1A-1H are tables depicting exemplary solvent systems and solubilites of various diazepine-containing formulations.

SUMMARY OF THE INVENTION

The present invention is directed to compositions and methods of formulating intranasal liquid medications that include a benzodiazepine-type anti-convulsive compound in an aqueous, single phase, multi-component solvent system having a water content of at least 15 vol % and a concentration of the anti-convulsive compound of at least 30 mg/ml. Most preferably, the anti-convulsive compound remains chemically stable and substantially completely dissolved in the composition at room temperature (20° C.) over an extended period (typically at least one week, and even more typically at least one month). The water content in contemplated formulations is preferably at least 15 vol %, more preferably at least 20 vol %, even more preferably at least 25 vol %, and most preferably at least 30 vol %, while allowing for a concentration of the benzodiazepine anti-convulsive compound at least 30 mg/ml, and more preferably at least 40 mg/ml at a sufficiently low viscosity to allow atomization of the solvent system in a fine droplet spray.

In one aspect of the inventive subject matter, a pharmaceutical composition is formulated for intranasal administration in a liquid form comprising a benzodiazepine (e.g., diazepam) anti-convulsive compound in an aqueous, single phase, multi-component solvent system with a water content of at least 15% by volume, wherein the anti-convulsive compound is present at a concentration of at least 30 mg/ml, and wherein the compound is chemically stable and remains substantially completely dissolved in the composition at room temperature over a period of at least 24 hours.

In especially preferred aspects, the anti-convulsive compound is a benzodiazepine-type compound (i.e., includes a substituted benzodiazepine ring system) and is diazepam, midazolam, flurazepam, triazolam, and/or alprazolam, and the single phase solvent system comprises at least three chemically distinct solvents. Among other suitable solvents, preferred solvents include N-methylpyrrolidone (NMP), acetone, anisole, dimethylacetamide (DMA), dimethylformamide (DMF), pyrrolidone, tetrahydrofuran (THF), benzyl benzoate, an alkyl lactate, a glycofurol, a short chain alcohol, a polyethylene glycol (PEG), propylene glycol, polyoxyl castor oil, glycerol, almond oil, cyclodextrin, a polyvinyl alcohol, and propylene carbonate. Particularly preferred solvent systems include N-methylpyrrolidone, an alcohol (e.g., ethanol), and a polyethylene glycol (e.g., PEG-200), most preferably at concentrations of between 15-35 vol %, between 25-50 vol %, and between 3-30 vol %, respectively. In yet further preferred aspects, the water content is at least 20 vol %, and even higher (e.g., at least 25 vol %). Additionally, compositions may further comprise one or more surfactants. It should be especially noted that despite the high water content and generally hydrophobic nature of the benzodiazepine compounds, the anti-convulsive compounds remain chemically stable and substantially completely dissolved over relatively long periods of time (e.g., more than 1 week, 1 month, and most typically 12 months) under normal storage conditions (e.g., room temperature).

Therefore, in another aspect of the inventive subject matter, it should be appreciated that a method of increasing a concentration of a benzodiazepine anti-convulsive compound in an aqueous, single phase, multi-component solvent system will include a step of increasing the water concentration in the multi-component solvent system to at least 15% by volume to achieve a concentration of the anti-convulsive compound of at least 30 mg/ml. Most preferably, the components of the solvent system are selected such that the increase in the water concentration allows the compound to remain chemically stable and substantially completely dissolved in the system at room temperature over a period of at least 24 hours. With respect to the solvent system, preferred components, ranges, and other conditions, the same considerations as provided above apply.

Consequently, the inventors also contemplate a pharmaceutical product for use in control of seizures that includes the formulation presented herein. Most advantageously, the product is configured as a nasal spray bottle (for single or multiple delivery of a measured spray volume), and the single phase solvent system comprises N-methylpyrrolidone, an alcohol (preferably ethanol), and a polyethylene glycol (preferably PEG-200). In such products, the anti-convulsive compound is preferably present at a concentration of at least 35 mg/ml, and the bottle is designed to allow administration of a single dose of atomized spray (i.e., average droplet size between 10 to 500 micron, and more typically between 20 to 120 micron) at a volume of equal or less than 150 μl of the composition. Of course, it should be noted that the term 'nasal spray bottle' as used herein also includes all other known devices for nasal administration that produce an atomized spray (e.g., pre-filled syringe with atomization tip, disposable spray blisters, etc.).

Various objects, features, aspects and advantages of the present invention will become more apparent from the following detailed description of preferred embodiments of the invention.

DETAILED DESCRIPTION

Numerous currently known benzodiazepine solutions are often either chemically instable, suffer from phase separation, and/or provide insufficient concentration of the benzodiazepine to be therapeutically effective for intranasal administration. For example, a single dose of 10 to 15 mg diazepam is typically appropriate to calm a normal adult suffering from an epileptic seizure. As the maximum liquid volume that can be delivered as atomized nasal spray without significant losses due to inhalation and/or out-dripping is about 150 μl per nostril, a concentration of about 40 mg/ml of diazepam is required. However, such concentrations cannot be achieved with water as the solvent (the solubility of diazepam in water at room temperature is about 0.9 mg/ml), and other many other known solvent systems are unsuitable as they do not allow atomized delivery, include pharmacologically unacceptable solvents, and/or fail to support sufficiently high concentration of the benzodiazepine. Therefore, intranasal administration of benzodiazepine anti-convulsive agents at therapeutically effective dosages from sufficiently stable formulations has not been achieved.

In contrast, the inventor has now unexpectedly discovered that a single phase solution of various solvents can be prepared in which various benzodiazepine compounds (e.g., diazepam, midazolam, etc.) can be completely dissolved at relatively high concentrations (e.g., at least 20 mg/ml, more typically at least 30 mg/ml, most typically at least 35-40 mg/ml). Moreover, such solutions will remain stable, will not separate into distinct phases, solubilize benzodiazepine compounds at remarkably high concentrations, and allow delivery in the form of an atomized spray for intranasal delivery. The term "single phase solution" as used herein refers to a solution that includes at least two chemically distinct solvents in which the solvents form a mixture without visually apparent phase formation (emulsion or phase separation) and in which the solvents remain in the mixture without visually apparent phase formation over at least 24 hours at room temperature and atmospheric pressure. As further used herein, the terms "benzodiazepine anti-convulsive compound" and "benzodiazepine" are used interchangeably herein and refer to all anti-convulsive compounds that include a substituted benzodiazepine moiety in the compound.

In one especially preferred aspect of the inventive subject matter, it is contemplated that a pharmaceutical composition has a liquid form of a benzodiazepine compound in an aqueous, single phase, multi-component solvent system with a water content of at least 15% by volume and the anti-convulsive compound at a concentration of at least 30 mg/ml of the composition, wherein the compound is chemically stable and remains substantially completely dissolved in the composition at room temperature over a period of at least 24 hours. Moreover, the viscosity of preferred compositions is sufficiently low to allow administration in an atomized spray. While diazepam and midazolam are particularly preferred benzodiazepine compounds, alternative compounds including flurazepam, triazolam, alprazolam, bromazepan, lorazepam, clonazepam, temazepam, oxazepam, flunitrazepam, chlordiazepoxide, estazolam, lormetazepam, nitrazepam, and mexazolam are also deemed suitable for use herein.

For example, one preferred formulation comprises 15-35 vol % N-methylpyrrolidone (and especially 30 vol % (+/−1)), 25-50 vol % of a short chain alcohol (and especially 30 vol % (+/−1) ethanol), 3-30 vol % of a polyethylene glycol (and especially 5 vol % (+/−1) PEG-200), 5-15 vol % polyoxyethylene castor oil (and especially 9.5 vol % (+/−1)), and water at a concentration of between 20-30 vol % (and especially 25 vol % (+/−1)). Remarkably, such and other multi-component solvent systems support benzodiazepine compound concentrations of up to 40 mg/ml and even higher without phase separation while providing an environment that allows for chemical stability. Moreover, such and similar solvent systems also exhibited sufficiently low viscosity to allow atomization of the fluid with average droplet sizes between 10 and 800, and more typically between 20 and 500, and most typically between 20 and 150 micron. Consequently, the formulations according to the inventive subject matter allowed atomized spray administration of a solution that had a concentration of at least 20 mg/ml, more typically at least 30 mg/ml, even more typically at least 35 mg/ml, and most typically at least 40 mg/ml of a benzodiazepine.

In preferred aspects of the inventive subject matter, the contemplated compositions will include solvents that are adequately tolerated (non-irritating), are pharmaceutically acceptable, and most preferably, are recognized in the US as "GRAS" (generally recognized as safe). Such solvents may also be listed in the FDA's database of acceptable inactive ingredients. With respect to the water content, it is generally preferred that the water concentration is chosen as high as possible to reduce the amount of organic solvents in the formulation. Therefore, preferred compositions will have at least 10 vol % water, more typically at least 20 vol %, and even more typically at least 25-30 vol % water in a solvent system in which the benzodiazepine derivative has a concentration of between about 20-40 mg/ml. As used herein, the term "about" in conjunction with a numeral refers to that numeral plus an absolute deviation of 10%, inclusive. For example, the term "about 10%" refers to a numeric range of between 9% and 11%, inclusive. In still further preferred aspects, and where desired, a non-ionic surfactant (e.g., polyoxyethylene castor oil derivative) may be added to the composition. Similarly, solvents may also act as absorption enhancers (e.g., NMP or polyoxyethylene castor oil components).

However, it should be recognized that numerous solvents other than NMP, polyethylene glycol, polyoxyethylene castor oil, and ethanol are also deemed suitable for use herein. Among other solvents, it is contemplated that appropriate compounds also include acetone, anisole, dimethylacetamide, dimethylformamide, pyrrolidone, tetrahydrofuran, benzyl benzoate, an alkyl (typically C1-C5) lactate, a glycofurol, a short chain (typically C1-C5) alcohol, a polyethylene glycol (typically those that are in liquid phase at room temperature [e.g., average molecular weight between 100 and 1500]), propylene glycol, polyoxyl castor oil (e.g., 30% polyoxyl castor oil, 10% polyoxyl castor oil), glycerol (e.g., glycerin-H, glycerin-F), almond oil, a cyclodextrin, a polyvinyl alcohol, and propylene carbonate.

While single solvents could theoretically be employed (see table below), it is generally preferred that multi-component solvent systems are used in conjunction with the teachings presented herein in which the quantity of non-water ingredients is reduced to reduce the possibility of irritation, and/or improve the ability to atomize the formulation. Therefore, generally preferred multi-solvent systems include those having (in addition to water) at least two, more preferably three, and most preferably four or more solvents. Additionally, surfactants (e.g., ionic and non-ionic surfactants) may also be included. In particularly preferred aspects of the inventive subject matter, acceptable solvents will have a regulatory status acceptable to U.S. FDA, thus relieving the requirement and risk of safety studies for the solvents. Table 1 below shows a list of exemplary solvents that can be used in the formulation, their solubility for diazepam, and their regulatory status:

TABLE 1

| No | Solvent | Solubility (mg/ml) | Regulatory Status |
|---|---|---|---|
| 1 | NMP, N-methylpyrrolidone | >500 | FDA listed inactive ingredient |
| 2 | Acetone | >100 | FDA listed inactive ingredient |
| 3 | Anisole | >100 | Not FDA listed |
| 4 | Dimethylacetaminde, DMA | >100 | Not FDA listed |
| 5 | Dimethylformamide, DMF | >100 | Not FDA listed |
| 6 | Dimethylsulfoxide, DMSO | >100 | FDA listed inactive ingredient |
| 7 | Pyrrolidone, 2-pyrrolidone | >100 | FDA listed inactive ingredient |
| 8 | Tetrahydrofuran, THF | >100 | Not FDA listed |
| 9 | benzyl benzoate | >100 | FDA listed inactive ingredient |
| 10 | Ethyl Lactate | 163 | FDA/GRAS listed |
| 11 | Propyl Lactate | 102 | Not FDA listed |
| 12 | Methyl Lactate | 97 | Not FDA listed |
| 13 | Butyl Lactate | 94 | Not FDA listed |
| 14 | Glycofurol | 84 | Not FDA listed |
| 15 | Ethylhexyl Lactate | 50 | Not FDA listed |
| 16 | Ethanol | 42 | FDA listed inactive ingredient |
| 17 | Methanol | 41 | FDA listed inactive ingredient |
| 18 | Polyethylene glycol | 30 | FDA listed inactive ingredient |
| 19 | Butanol, 1-butanol | 29 | Not FDA listed |
| 20 | Propylene gycol | 16 | FDA listed inactive ingredient |
| 21 | 30% Polyoxyl castor oil | 5 | FDA listed inactive ingredient |
| 22 | 10% Polyoxyl castor oil | 2 | FDA listed inactive ingredient |
| 23 | Glycerin-H. | 1.5 | FDA/GRAS listed |
| 24 | Water | 0.9 | Included in non-parenteral and parenteral medications |
| 25 | Almond Oil, NF/USP | Negligible | Included in non-parenteral and parenteral medications |
| 26 | Cyclodextrin solution | Negligible | FDA listed inactive ingredient |
| 27 | Glycerin-F | Negligible | FDA/GRAS listed |
| 28 | Polyvinyl alcohol | Negligible | FDA listed inactive ingredient |
| 29 | Propylene carbonate | Negligible | FDA listed inactive ingredient |

Thus, based on the experimental data (infra) and contrary to the expectation based on Table 1 above, it should be noted that the concentration of a benzodiazepine anti-convulsive compound in an aqueous, single phase, multi-component solvent system can be increased by increasing the water concentration in the multi-component solvent system to at least 15 vol % such that the concentration of the anti-convulsive compound is at least 30 mg/ml (and more typically at least 35 mg/ml, and most typically at least 40 mg/ml). In such contemplated methods, the components of the solvent system are selected such that the step of increasing the water concentration allows the compound to remain chemically stable and substantially completely dissolved in the system at room temperature over a period of at least 24 hours, more typically at least 1 week, even more typically at least one month, and most typically at least 1 year. With respect to most preferred solvent systems, the same considerations as provided above apply. Therefore, especially suitable solvent systems include those comprising water (typically at least 15 vol %) and a mixture of at least two or three of N-methylpyrrolidone, acetone, anisole, dimethylacetamide, dimethylformamide, pyrrolidone, tetrahydrofuran, benzyl benzoate, an alkyl lactate, a glycofurol, a short chain alcohol, a polyethylene glycol, propylene glycol, polyoxyl castor oil, glycerol, almond oil, cyclodextrin, a polyvinyl alcohol, and propylene carbonate. For example, especially suitable solvent systems will include at least 15 vol % water, a polyethylene glycol (e.g., PEG 200), N-methylpyrrolidone, and a short chain alcohol. Additionally, such systems will also include polyoxyethylene castor oil.

Remarkably, many of the contemplated formulations provided excellent solubility for the benzodiazepine compound while maintaining chemical stability (i.e., benzodiazepine is not degraded or fails to react otherwise with the solvent). Therefore, the term "remains chemically stable" in conjunction with the benzodiazepine compound means that at least 95 mol % of the benzodiazepine compound remains chemically unchanged after storage in the solvent system at room temperature over a period of at least 7 days. Similarly, the term "remains substantially completely dissolved" as used herein means that at least 95 mol % of the benzodiazepine compound remains dissolved in the solvent system after storage in the solvent system at room temperature over a period of at least 7 days.

Consequently, it should be appreciated that is now possible to formulate anti-convulsive medication in a prepackaged form in which contemplated formulations are packaged in a nasal spray bottle (e.g., single use per nostril, or multiple uses). Most advantageously, the bottle will be configured to allow administration of a single dose of atomized spray at a volume of equal or less than 150 μl of the composition having a benzodiazepine concentration of at least 30-30 mg/mg to so achieve a fast and effective dosage for intranasal administration.

With respect to suitable information for use and/or administration of contemplated compositions, it is preferred that the information may be in displayed, printed, or otherwise visually presented form (e.g., in a sales flyer, an Internet advertisement, etc.). Alternatively, or additionally, the information may also be in an audible format, including radio advertisements, talk shows, infomercials, etc.). Most preferably, the information is in printed format and associated with the pharmaceutical product. For example, the information may be provided as a packaging insert, or be printed on the container that includes the pharmaceutical product. In further contemplated aspects, the information may further provide information that the combination is effective as a therapeutic agent in the treatment of seizures, and especially in the treatment of epileptic seizures.

EXPERIMENTS

Figure 1G:
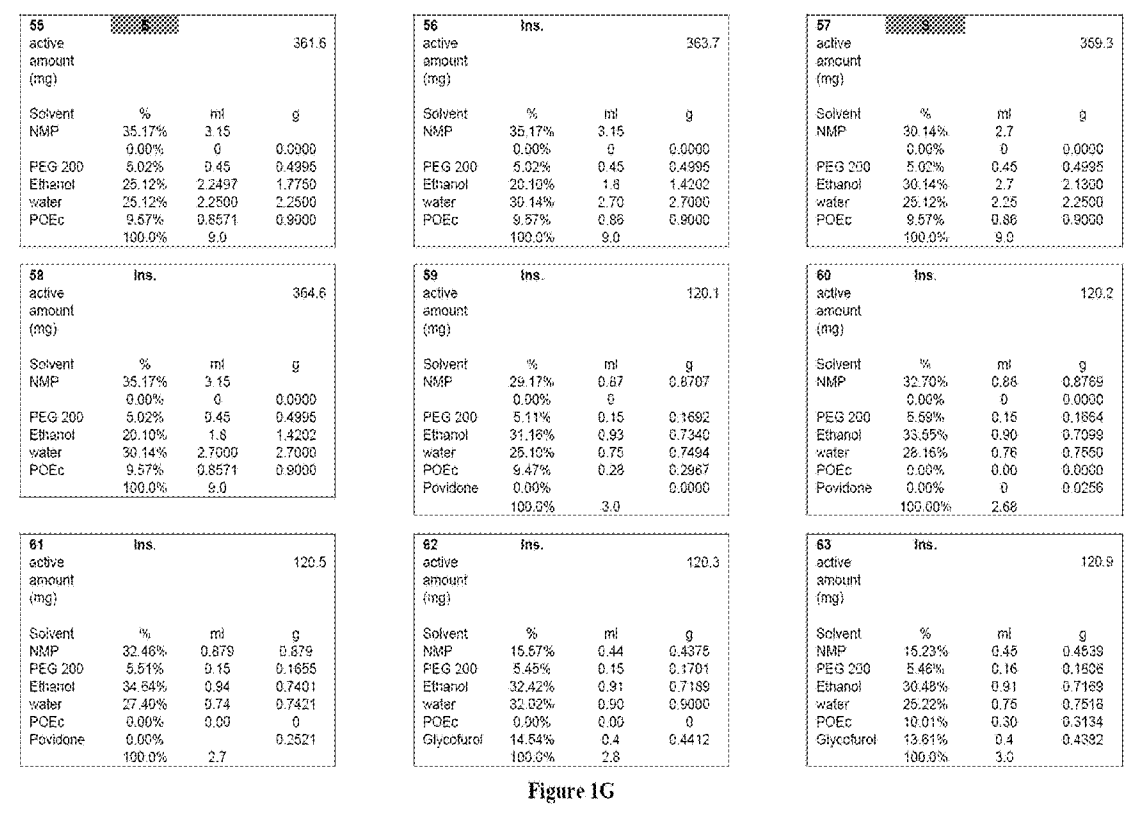

The following examples are provided to demonstrate that significant benzodiazepine concentrations can be achieved using multi-solvent systems with unexpected and relatively high water content. Most remarkably, various solvent systems with benzodiazepine concentrations of 40 mg/ml could be prepared in which the water content was as high as 30 vol %. At least some of such systems provided a stable single phase solvent in which the diazepam remained dissolved over prolonged periods of storage. In many cases, the benzodiazepine remained chemically stable and substantially completely dissolved in solvent system at room temperature over a period of at least 1 week (although longer storage periods were also recorded). Exemplary s solvent systems and results are depicted in the tables of FIGS. 1A-1H in which Ins. denotes insoluble, S denotes soluble, and S/NCS denotes soluble, but not chemically stable. PEG 200 denotes polyethylene glycol 200, POEc denotes polyoxyethylene castor oil, NMP denotes N-methyl-pyrrolidone, Pr. Glycol denotes propylene glycol, Eth. Lact. denotes ethyl lactate.

Based on the experimental formulations shown in the Figures and other data (not shown), it appears that about 30 vol % water is the upper limit for benzodiazepine concentrations of about 40 mg/ml with respect to long-term stability and/or solubility. Thus, while water concentrations of 30 vol % are expressly contemplated herein, lower concentrations (typically between 20 and 30 vol %) are generally preferred. Solvents with structures containing acyclic ketones and esters were found to chemically react with the benzodiazepine, causing impurities to form. Therefore, while ethyl lactate is conceptually a desirable solvent with regard to its capability to solubilize benzodiazepine, ethyl lactate may form impurities. Among other desirable formulations, the solvent system 57 on FIG. 1G provided the most benefits.

Thus, specific embodiments and applications of intranasal benzodiazepine formulations have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Furthermore, where a definition or use of a term in a reference, which is incorporated by reference herein is inconsistent or contrary to the definition of that term provided herein, the definition of that term provided herein applies and the definition of that term in the reference does not apply.

What is claimed is:
1. A method of increasing a concentration of a diazepam in an aqueous, single phase, multi-component solvent system, comprising:
increasing a water concentration in the multi-component solvent system to at least 15% by volume such that the concentration of the diazepam is at least 30 mg/ml; and
wherein the components of the solvent system are selected such that the step of increasing the water concentration allows the diazepam to remain chemically stable and substantially completely dissolved in the system at room temperature over a period of at least 24 hours; and
wherein the multi-component solvent system is selected from the group consisting of
(a) N-methylpyrrolidone in an amount of about 15 vol %, ethanol in an amount of about 50 vol %, and PEG-200 in an amount of about 20 vol %,
(b) N-methylpyrrolidone in an amount of about 20 vol %, ethanol in an amount of about 45 vol %, and PEG-200 in an amount of about 15 vol %,
(c) N-methylpyrrolidone in an amount of about 20 vol %, ethanol in an amount of about 45 vol %, and PEG-200 in an amount of about 17.5 vol %,
(d) N-methylpyrrolidone in an amount of about 50 vol %, ethanol in an amount of about 0 vol %, and PEG-200 in an amount of about 50 vol %,

(e) N-methylpyrrolidone in an amount of about 35.2 vol %, ethanol in an amount of about 25.1 vol %, and PEG-200 in an amount of about 5.0 vol %, and (f) N-methylpyrrolidone in an amount of about 30.1 vol %, ethanol in an amount of about 30.1 vol %, and PEG-200 in an amount of about 5.0 vol %.

2. The method of claim 1 wherein the water concentration is increased to at least 20 vol % and wherein the concentration of the anti-diazepam is at least 35 mg/ml.

3. The method of claim 1 wherein the components of the solvent system are selected such as to allow the compound to remain chemically stable and substantially completely dissolved in the system at room temperature over a period of at least 2 months.

4. An aqueous pharmaceutical composition formulated for intranasal administration in atomized spray form having an average droplet size between 20 and 150 micron, the composition comprising:

diazepam in an aqueous, single phase, multi-component solvent system with a water content of at least 15% by volume and the diazepam at a concentration of at least 30 mg/ml of the composition;

wherein the multi-component solvent system is selected from the group consisting of (a) N-methylpyrrolidone in an amount of about 15 vol %, ethanol in an amount of about 50 vol %, and PEG-200 in an amount of about 20 vol %, (b) N-methylpyrrolidone in an amount of about 20 vol %, ethanol in an amount of about 45 vol %, and PEG-200 in an amount of about 15 vol %, (c) N-methylpyrrolidone in an amount of about 20 vol %, ethanol in an amount of about 45 vol %, and PEG-200 in an amount of about 17.5 vol %, (d) N-methylpyrrolidone in an amount of about 50 vol %, ethanol in an amount of about 0 vol %, and PEG-200 in an amount of about 50 vol %, (e) N-methylpyrrolidone in an amount of about 35.2 vol %, ethanol in an amount of about 25.1 vol %, and PEG-200 in an amount of about 5.0 vol %, and (f) N-methylpyrrolidone in an amount of about 30.1 vol %, ethanol in an amount of about 30.1 vol %, and PEG-200 in an amount of about 5.0 vol %.

5. A nasal spray bottle comprising the pharmaceutical composition of claim 4.

6. The spray bottle of claim 5 wherein the bottle is configured to allow administration of a single dose of atomized spray at a volume of equal or less than 150 µl of the composition.

7. The aqueous pharmaceutical composition of claim 4 wherein the diazepam is present at a concentration of at least 35 mg/ml of the composition.

* * * * *